United States Patent
Chan et al.

(10) Patent No.: US 9,691,214 B2
(45) Date of Patent: Jun. 27, 2017

(54) ENVIRONMENTALLY ADAPTIVE OLFACTORY GENERATION

(71) Applicant: INTERNATIONAL BUSINESS MACHINES CORPORATION, Armonk, NY (US)

(72) Inventors: Yuk L. Chan, Rochester, NY (US); Michael D. Essenmacher, Danbury, CT (US); David B. Lection, Raleigh, NC (US); Eric L. Masselle, Raleigh, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/930,713

(22) Filed: Nov. 3, 2015

(65) Prior Publication Data

US 2017/0124797 A1     May 4, 2017

(51) Int. Cl.
    *G07F 17/00*     (2006.01)
    *A61L 9/14*      (2006.01)

(52) U.S. Cl.
    CPC ............ *G07F 17/0014* (2013.01); *A61L 9/14* (2013.01); *A61L 2209/11* (2013.01); *A61L 2209/111* (2013.01)

(58) Field of Classification Search
    CPC .. A61L 2209/11; A61L 2209/111; A61L 9/11; A61L 9/14; A61L 9/03; A61L 9/032; A61L 9/035; B05B 12/12
    See application file for complete search history.

(56) References Cited

U.S. PATENT DOCUMENTS

| | | | |
|---|---|---|---|
| 8,881,999 B2* | 11/2014 | Blaylock | A61L 9/122 239/337 |
| 9,439,995 B2* | 9/2016 | Conroy | B05B 7/2416 |
| 2005/0208673 A1 | 9/2005 | Labreche et al. | |
| 2011/0253797 A1* | 10/2011 | Weening | A61L 9/14 239/1 |
| 2013/0081541 A1* | 4/2013 | Hasenoehrl | A61L 9/035 96/222 |
| 2014/0060452 A1 | 3/2014 | Linssen et al. | |

(Continued)

OTHER PUBLICATIONS

Disclosed Anonymously "Portable electronic device with chemical sensor", Publication: Feb. 3, 2014; IP.com No. 000234766; 31 pgs.

(Continued)

*Primary Examiner* — Timothy Waggoner
(74) *Attorney, Agent, or Firm* — Cantor Colburn LLP; William A. Kinnaman, Jr.

(57) ABSTRACT

Embodiments include environmentally adaptive olfactory generation systems and methods and computer program products for operating the same. Aspects include receiving a desired concentration of an olfactory stimulant, receiving a detected concentration of the olfactory stimulant from an olfactory stimulant sensor, and receiving one or more environmental factors from an environmental sensor. Aspects also include comparing the detected concentration of the olfactory stimulant with the desired concentration of the olfactory stimulant and adjusting a dispensing characteristic of an olfactory stimulant emitter based on the comparison and the one or more environmental factors.

14 Claims, 3 Drawing Sheets

(56) References Cited

U.S. PATENT DOCUMENTS

2014/0201182 A1    7/2014  Amin et al.
2015/0019030 A1*   1/2015  Chandler ............. G05D 7/0629
                                                                700/283
2015/0297779 A1*  10/2015  Conroy ................ B05B 7/2416
                                                                239/1

OTHER PUBLICATIONS

IBM; Gerber et al., "Scent Generator" IBM Technical Disclosure Bulletin, vol. 38, No. 11, Nov. 1, 1995; IP.com No. 000116913; 3 pgs.
Shurmer, H.V., "The fifth sense on the science of the electronic nose", IEE Review Mar. 1990, pp. 95-98.

* cited by examiner

ENVIRONMENTALLY ADAPTIVE OLFACTORY GENERATION

BACKGROUND

The present disclosure relates to olfactory generation and more specifically, to environmentally adaptive olfactory generation systems and methods for operating the same.

In general, olfactory generation systems are used to convey a desired scent to an individual. Such olfactory generation systems can be used to increase the depth of a user experience by adding olfactory stimulation to other types of stimulation, such as audio and video. Olfactory generation systems are used for various commercial applications including advertising campaigns, marketing campaigns and entertainment applications. One well-known example of an olfactory generation system being used in a marketing campaign is the use of bakery and coffee scents used in coffee shops. Another example of olfactory generation systems is a television system that has been configured to provide a sense of smell to its viewers.

While various olfactory generation systems have been developed, their effectiveness, and therefore their adoption, has been limited due to various technical limitations.

SUMMARY

In accordance with an embodiment, a method for environmentally adaptive olfactory generation is provided. The method includes receiving a desired concentration of an olfactory stimulant, receiving a detected concentration of the olfactory stimulant from an olfactory stimulant sensor, and receiving one or more environmental factors from an environmental sensor. The method also includes comparing the detected concentration of the olfactory stimulant with the desired concentration of the olfactory stimulant and adjusting a dispensing characteristic of an olfactory stimulant emitter based on the comparison and the one or more environmental factors.

In accordance with another embodiment, an environmentally adaptive olfactory generation system includes a processor in communication with a memory. The processor is configured to receive a desired concentration of an olfactory stimulant, receive a detected concentration of the olfactory stimulant from an olfactory stimulant sensor, and receive one or more environmental factors from an environmental sensor. The processor is also configured to compare the detected concentration of the olfactory stimulant with the desired concentration of the olfactory stimulant and adjust a dispensing characteristic of an olfactory stimulant emitter based on the comparison and the one or more environmental factors.

In accordance with a further embodiment, a computer program product for environmentally adaptive olfactory generation includes a non-transitory storage medium readable by a processing circuit and storing instructions for execution by the processing circuit for performing a method. The method includes receiving a desired concentration of an olfactory stimulant, receiving a detected concentration of the olfactory stimulant from an olfactory stimulant sensor, and receiving one or more environmental factors from an environmental sensor. The method also includes comparing the detected concentration of the olfactory stimulant with the desired concentration of the olfactory stimulant and adjusting a dispensing characteristic of an olfactory stimulant emitter based on the comparison and the one or more environmental factors.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

In accordance with exemplary embodiments of the disclosure, methods, systems and computer program products for environmentally adaptive olfactory generation are provided. In exemplary embodiments, an environmentally adaptive olfactory generation system is configured to monitor a level of an olfactory stimulant at a location of a user and to responsively control the operation of an olfactory stimulant emitter to ensure that the olfactory stimulant concentration at the location is a desired olfactory stimulant concentration. In exemplary embodiments, the environmentally adaptive olfactory generation system is configured to adjust the operation of an olfactory stimulant emitter based on detected environmental factors, which may include distance between the olfactory stimulant emitter and the location, air movement intensity and direction, a humidity level, and a temperature.

Figure 1:
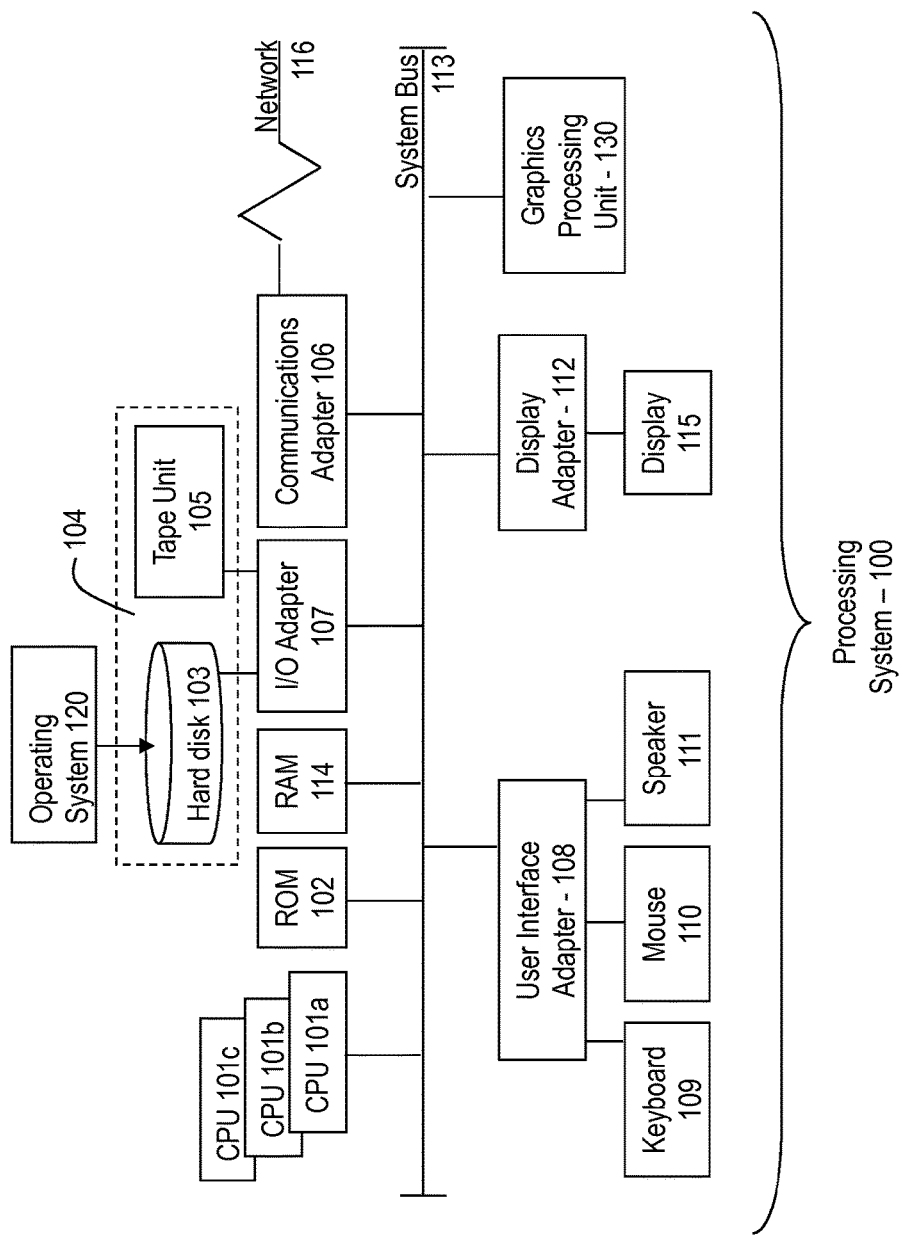
FIG. 1 is a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101*a*, 101*b*, 101*c*, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112. A keyboard 109, mouse 110, and speaker 111 all interconnected to bus 113 via user interface adapter 108, which may include, for example, a Super I/O chip integrating multiple device adapters into a single integrated circuit.

In exemplary embodiments, the processing system 100 includes a graphics processing unit 130. Graphics processing unit 130 is a specialized electronic circuit designed to manipulate and alter memory to accelerate the creation of images in a frame buffer intended for output to a display. In general, graphics processing unit 130 is very efficient at manipulating computer graphics and image processing, and has a highly parallel structure that makes it more effective than general-purpose CPUs for algorithms where processing of large blocks of data is done in parallel.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system to coordinate the functions of the various components shown in FIG. 1.

Figure 2:
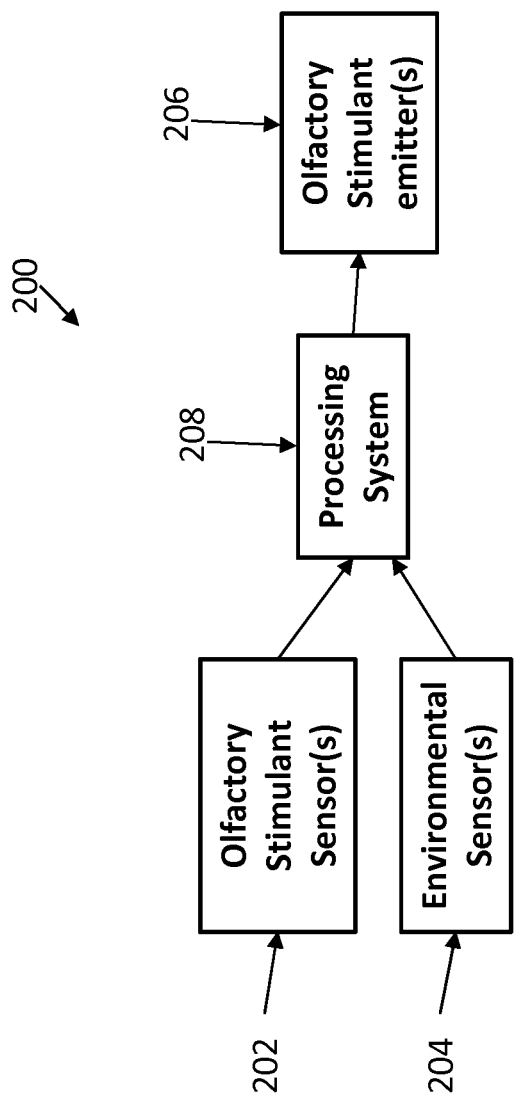
FIG. 2 is a block diagram illustrating an environmentally adaptive olfactory generation system in accordance with an exemplary embodiment.

Referring to FIG. 2, there is shown a block diagram of an embodiment of an environmentally adaptive olfactory system 200. As illustrated, environmentally adaptive olfactory system 200 includes a processing system 208, which may be a processing system similar to the one described above with reference to FIG. 1. The environmentally adaptive olfactory system 200 also includes one or more olfactory stimulant sensors 202, one or more environmental sensors 204 and one or more olfactory stimulant emitters 206, which are all in communication with the processing system 208. Although the processing system 208, the olfactory stimulant sensor 202, the environmental sensor 204 and the olfactory stimulant emitter 206 are illustrated as separate devices, it will be understood by those of ordinary skill in the art that one or more, or in some cases all, of these device may be disposed in a single device. A detailed discussion of the composition of the olfactory stimulant sensor 202, the environmental sensor 204 and the olfactory stimulant emitter 206 is not included herein as these elements are well-known in the existing art.

In exemplary embodiments, the olfactory stimulant sensor 202 is configured to detect a concentration level of one or more olfactory stimulants in the air. The olfactory stimulant sensor 202 may include any of a wide variety of known sensor technologies that are configured to detect a concentration level of one or more olfactory stimulants in the air. In exemplary embodiments, the environmentally adaptive olfactory system 200 may include a plurality of olfactory stimulant sensors 202 that are located in various locations. For example, in an olfactory stimulant system 200 that includes a television having an olfactory stimulant emitter 206, an olfactory stimulant sensor 202 may be disposed at a location where a user will be watching the television. The olfactory stimulant sensor 202 is configured to provide the processing system 208 with the detected concentration level of one or more olfactory stimulants in the air. In exemplary embodiments. The olfactory stimulant sensor 202 and the processing system 208 may communicate using any of a variety of known wireless communications protocols.

In exemplary embodiments, the olfactory stimulant emitter 206 is configured to dispense one or more olfactory stimulants. The olfactory stimulant emitter 206 has one or more dispensing characteristics that can be adjusted. The dispensing characteristics include, but are not limited to, a concentration of the olfactory stimulant that is dispensed, an amount of the olfactory stimulant that is dispensed, an orientation of the olfactory stimulant emitter, and a rate that the olfactory stimulant is dispensed.

In exemplary embodiments, the processing system 208 receives a detected olfactory stimulant concentration from the olfactory stimulant sensor 202 and compares the detected concentration with the desired concentration. Based on determining that the detected concentration is greater than a desired concentration, the processing system 208 will instruct the olfactory stimulant emitter 206 to decrease a rate or a concentration of the olfactory stimulant emitted. Based on determining that the detected concentration is less than a desired concentration, the processing system 208 will instruct the olfactory stimulant emitter 206 to increase a rate or a concentration of the olfactory stimulant emitted.

In exemplary embodiments, the processing system 208 is configured to create a mapping of the concentration of the olfactory stimulant detected, which can include an indication of the concentration of the olfactory stimulant emitted. For example, the mapping may include a graphical representation of the concentrations of the olfactory stimulant detected by various olfactory stimulant sensors 202, which includes a spatial representation of the area in which the olfactory stimulant sensors 202 and the olfactory stimulant sensor 202 are disposed. This mapping may be continuously updated based on the latest detected olfactory stimulant concentration, and the mapping can be used to determine an amount, or concentration of an olfactory stimulant to dispense based on the desired concentration. In exemplary embodiments, the mapping collected from one user/configuration can be made available to other users, where an olfactory stimulant sensor might not be available. Each mapping may also contain environmental factors such as humidity, air flow, air temperature, GPS locations, and the like. These environmental factors can be used to determine how much olfactory stimulant to dispense, particularly when an olfactory stimulant sensor is not available.

In one embodiment, an olfactory stimulant emitter is used by a store in a shopping mall and one or more smartphones of shoppers in the mall include an olfactory stimulant sensor. The store also includes a processing system that is configured to receive detected olfactory stimulant concentrations from the smartphones of the users. The processing system is configured to use a known indoor location technology to determine a location of the smartphones with respect to the olfactory stimulant emitter. Based on the locations of the smartphones and the detected olfactory stimulant concentrations, the processing system is configured to create a mapping of the olfactory stimulant concentrations in the store. The processing system can use this mapping and a desired olfactory stimulant concentration to responsively adjust the operation of the olfactory stimulant emitter in the store.

Figure 3:
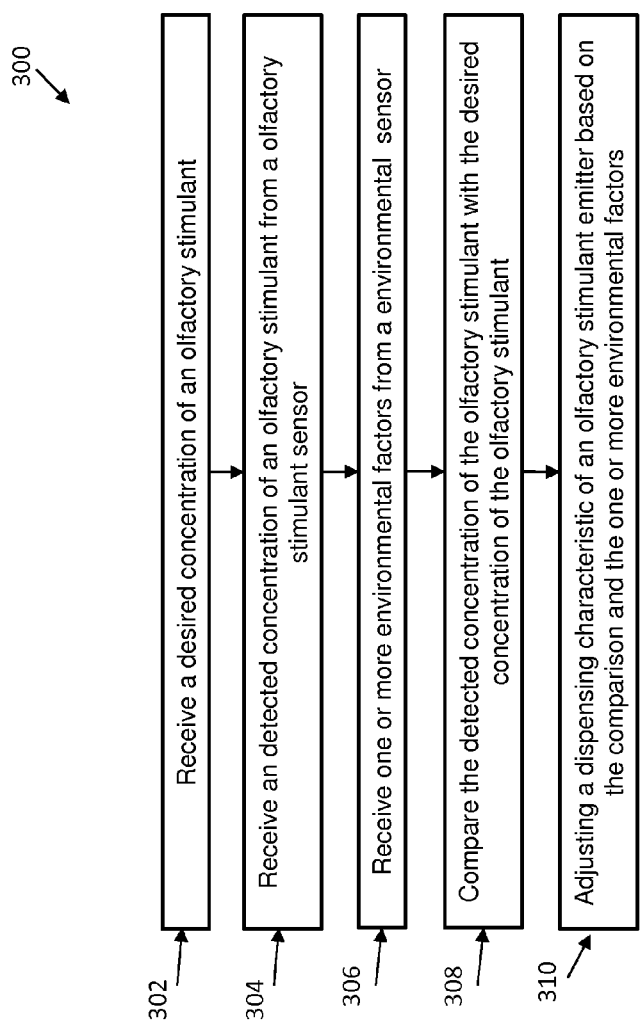
FIG. 3 is a flow diagram of a method for environmentally adaptive olfactory generation in accordance with an exemplary embodiment.

Referring now to FIG. 3, a flow diagram of a method 300 for environmentally adaptive olfactory generation in accordance with an exemplary embodiment is shown. As shown at block 302, the method 300 includes receiving a desired concentration of an olfactory stimulant. Next, as shown at block 304, the method 300 includes receiving a detected concentration of the olfactory stimulant from an olfactory stimulant sensor. The method 300 also includes receiving one or more environmental factors from an environmental sensor, as shown at block 306. In exemplary embodiments, the one or more environmental factors include a distance between an olfactory stimulant emitter and the olfactory stimulant sensor. The one or more environmental factors may also include one or more of humidity, an air flow, and a location of the olfactory stimulant sensor. Next, as shown at block 308, the method 300 also includes comparing, by a processor, the detected concentration of the olfactory stimulant with the desired concentration of the olfactory stimulant. The method 300 also includes adjusting a dispensing characteristic of an olfactory stimulant emitter based on the comparison and the one or more environmental factors, as shown at block 310. In exemplary embodiments, the dispensing characteristic includes one or more of a concentration of the olfactory stimulant that is dispensed, an amount of the olfactory stimulant that is dispensed, an orientation of the olfactory stimulant emitter, and a rate that the olfactory stimulant is dispensed.

In exemplary embodiments, the desired concentration of the olfactory stimulant can be calculated by adjusting a content provider olfactory concentration level based on a stored user profile created by a user. For example, a content provider, such as a film maker, may set a content provider olfactory concentration level for a scene of a movie based on a concentration of the olfactory stimulant needed to provide a desired effect to an average user. The film maker may determine a content provider olfactory concentration level by surveying multiple individuals. The user profile may be used to adjust the content provider olfactory concentration level based on a sensitivity of a particular user to the olfactory stimulant. For example, a specific user may be more or less sensitive to a particular olfactory stimulant and require more or less of the olfactory stimulant to achieve a desired effect. The user profile can be used to store such information and to customize the olfactory generation system to each individual user.

In exemplary embodiments, the method 300 also includes creating a mapping of the detected concentration of the olfactory stimulant received from a plurality of olfactory stimulant sensors. In one embodiment, the mapping may be based on the distance from each of the plurality of olfactory stimulant sensors and the olfactory stimulant emitter and the dispensing characteristics. In another embodiment, the mapping may be based on the one or more environmental factors and the dispensing characteristics.

In exemplary embodiments, the olfactory stimulant emitter, the olfactory stimulant sensor and the processing system may be disposed on mobile computing device, such as a smartwatch or smartphone. The processing system may be configured to communicate with one or more external systems and the external systems may provide the processing system with signals indicative of an olfactory stimulant to emit. For example, there are many situations in which it is desirable to generate a scent with a mobile computing device, such as watching a movie on a smart phone, walking through a supermarket where various smell could be generated based an item being viewed by the user.

In one embodiment, a retail store may use an olfactory generation system to market a product to an individual. Based on environment factors of the retail store, the olfactory stimulant may reach different individuals at different concentrations. In such examples, users that have a mobile device having an olfactory stimulant emitter and olfactory stimulant sensor can detect the concentration of the olfactory stimulant and emit additional olfactory stimulants to "scale up" the olfactory stimulant concentration to a desired concentration, where the desired concentration is received from the olfactory generation system of the store.

In exemplary embodiments, the olfactory generation system can be configured to detect other olfactory scents in the environment and to responsively modifying the output of the stimulant emitter based an effect that the other olfactory scents in the environment that might have on the olfactory stimulant being emitted. For example, the olfactory generation system may detect a presence of a chemical in the environment that will react with an olfactory stimulant to produce an undesired odor. In response to detecting such a chemical in the environment, the olfactory generation system may be configured to change a type or concentration of olfactory stimulant emitted.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for environmentally adaptive olfactory generation, the method comprising:
   receiving a desired concentration of an olfactory stimulant;
   receiving a detected concentration of the olfactory stimulant from an olfactory stimulant sensor;
   receiving one or more environmental factors from an environmental sensor, wherein the one or more environmental factors include a distance between the olfactory stimulant emitter and the olfactory stimulant sensor;
   comparing, by a processor, the detected concentration of the olfactory stimulant with the desired concentration of the olfactory stimulant;
   adjusting a dispensing characteristic of an olfactory stimulant emitter based on the comparison and the one or more environmental factors, wherein the dispensing characteristic includes an orientation of the olfactory stimulant emitter; and
   creating, by the processor, a mapping of the detected concentration of the olfactory stimulant received from a plurality of olfactory stimulant sensors based on the distance from each of the plurality of olfactory stimulant sensors and the olfactory stimulant emitter and the dispensing characteristic.

2. The computer-implemented method of claim 1, wherein the one or more environmental factors include one or more of humidity, an air flow, and a location of the olfactory stimulant sensor.

3. The computer-implemented method of claim 2, further comprising creating, by the processor, a mapping of the detected concentration of the olfactory stimulant received from a plurality of olfactory stimulant sensors based on the one or more environmental factors and the dispensing characteristic.

4. The computer-implemented method of claim 1, wherein the dispensing characteristic includes one or more of a concentration of the olfactory stimulant that is dispensed, an amount of the olfactory stimulant that is dispensed, and a rate that the olfactory stimulant is dispensed.

5. The computer-implemented method of claim 1, wherein the desired concentration of the olfactory stimulant is calculated by adjusting a content provider olfactory concentration level based on a stored user profile created by a user.

6. A computer program product for environmentally adaptive olfactory generation, the computer program product comprising:
   a non-transitory storage medium readable by a processing circuit and storing instructions for execution by the processing circuit for performing a method comprising:
   receiving a desired concentration of an olfactory stimulant;
   receiving a detected concentration of the olfactory stimulant from an olfactory stimulant sensor, wherein the one or more environmental factors include a distance between the olfactory stimulant emitter and the olfactory stimulant sensor;

receiving one or more environmental factors from an environmental sensor;

comparing the detected concentration of the olfactory stimulant with the desired concentration of the olfactory stimulant;

adjusting a dispensing characteristic of an olfactory stimulant emitter based on the comparison and the one or more environmental factors, wherein the dispensing characteristic includes an orientation of the olfactory stimulant emitter; and creating, by the processor, a mapping of the detected concentration of the olfactory stimulant received from a plurality of olfactory stimulant sensors based on the distance from each of the plurality of olfactory stimulant sensors and the olfactory stimulant emitter and the dispensing characteristic.

7. The computer program product of claim 6, wherein the one or more environmental factors include one or more of humidity, an air flow, and a location of the olfactory stimulant sensor.

8. The computer program product of claim 7, wherein the method further comprises creating a mapping of the detected concentration of the olfactory stimulant received from a plurality of olfactory stimulant sensors based on the one or more environmental factors and the dispensing characteristic.

9. The computer program product of claim 6, wherein the dispensing characteristic includes one or more of a concentration of the olfactory stimulant that is dispensed, an amount of the olfactory stimulant that is dispensed and a rate that the olfactory stimulant is dispensed.

10. The computer program product of claim 6, wherein the desired concentration of the olfactory stimulant is calculated by adjusting a content provider olfactory concentration level based on a stored user profile created by a user.

11. An environmentally adaptive olfactory generation system comprising:

an olfactory stimulant sensor configured to detect an actual concentration of an olfactory stimulant;

an olfactory stimulant emitter configured to emit an olfactory stimulant;

an environmental sensor configured to detect one or more environmental factors, wherein the one or more environmental factors include a distance between the olfactory stimulant emitter and the olfactory stimulant sensor;

a processing system in communication with the olfactory stimulant sensor, the environmental sensor and the olfactory stimulant emitter, the processing system configured to:

compare the actual concentration of the olfactory stimulant with a desired concentration of the olfactory stimulant;

adjust a dispensing characteristic of the olfactory stimulant emitter based on the comparison and the one or more environmental factors, wherein the dispensing characteristic includes an orientation of the olfactory stimulant emitter; and create a mapping of the detected concentration of the olfactory stimulant received from a plurality of olfactory stimulant sensors based on the distance from each of the plurality of olfactory stimulant sensors and the olfactory stimulant emitter and the dispensing characteristic.

12. The environmentally adaptive olfactory generation system of claim 11, wherein the one or more environmental factors include one or more of humidity, an air flow, and a location of the olfactory stimulant sensor.

13. The environmentally adaptive olfactory generation system of claim 11, wherein the dispensing characteristic includes one or more of a concentration of the olfactory stimulant that is dispensed, an amount of the olfactory stimulant that is dispensed and a rate that the olfactory stimulant is dispensed.

14. The environmentally adaptive olfactory generation system of claim 11, wherein the desired concentration of the olfactory stimulant is calculated by adjusting a content provider olfactory concentration level based on a stored user profile created by a user.

\* \* \* \* \*